United States Patent [19]

Baker et al.

[11] Patent Number: 5,208,248
[45] Date of Patent: May 4, 1993

[54] INDAZOLE-SUBSTITUTED FIVE-MEMBERED HETEROAROMATIC COMPOUNDS

[75] Inventors: Raymond Baker; Mark S. Chambers, both of Hertfordshire; Leslie J. Street, Essex, all of England

[73] Assignee: Merck Sharpe & Dohme, Ltd., Hertfordshire, United Kingdom

[21] Appl. No.: 730,751

[22] Filed: Jul. 16, 1991

Related U.S. Application Data

[63] Continuation-in-part of Ser. No. 665,047, Mar. 6, 1991, abandoned.

[30] Foreign Application Priority Data

Jan. 11, 1991 [GB] United Kingdom ............... 9100648

[51] Int. Cl.$^5$ ................ C07D 413/10; A61K 31/415
[52] U.S. Cl. ................. 514/364; 546/199; 546/271; 548/128; 548/129; 548/131; 548/132; 548/133
[58] Field of Search ............... 514/364; 548/131, 132, 548/133; 546/199, 271

[56] References Cited

U.S. PATENT DOCUMENTS 5,140,034  8/1992  Baker .................. 514/364

Primary Examiner—Robert Gerstl
Attorney, Agent, or Firm—Robert J. North; Manfred Polk; Joseph F. DiPrima

[57] ABSTRACT

A class of indazole-substituted five-membered heteroaromatic compounds are specific agonists of 5-HT$_1$-like receptors and are therefore useful in the treatment of clinical conditions, in particular migraine and associated disorders, for which a selective agonist of these receptors is indicated.

7 Claims, No Drawings

INDAZOLE-SUBSTITUTED FIVE-MEMBERED HETEROAROMATIC COMPOUNDS

This is a continuation-in-part of U.S. application Ser. No. 665,047 filed Mar. 6, 1991 now abandoned.

The present invention relates to a class of indazole-substituted five-membered heteroaromatic compounds which act on 5-hydroxytryptamine (5-HT) receptors, being specific agonists of so-called "5-HT$_1$-like" receptors. They are therefore useful in the treatment of clinical conditions for which a selective agonist of these receptors is indicated.

5-HT$_1$-like receptor agonists which exhibit selective vasoconstrictor activity have recently been described as being of use in the treatment of migraine (see, for example, A. Doenicke et al., *The Lancet*, 1988, Vol. 1, 1309–11). The compounds of the present invention, being specific 5-HT$_1$-like receptor agonists, are accordingly of particular use in the treatment of migraine and associated conditions, e.g. cluster headache, chronic paroxysmal hemicrania and headache associated with vascular disorders.

EP-A-0313397 describes a class of tryptamine derivatives substituted by a five-membered heteroaliphatic ring, which are stated to act as specific agonists of a particular type of "5-HT$_1$-like" receptor and thus to be effective therapeutic agents for the treatment of clinical conditions, particularly migraine, requiring this activity. However, EP-A-0313397 neither discloses nor suggests the heteroaromatic compounds provided by the present invention.

EP-A-0328200 describes a class of 5-membered heterocyclic compounds having at least one heteroatom, substituted on the heterocyclic ring by an azacyclic or azabicyclic ring system or an amino substituent. These compounds are stated to be useful in the treatment of psychotic disorders (e.g. schizophrenia and mania); anxiety; alcohol or drug withdrawal; pain; gastric stasis; gastric dysfunction; migraine, nausea and vomiting; and presenile and senile dementia. However, they have no action on the 5-HT$_1$-like receptors of which the heteroaromatic compounds of the present invention are specific agonists, and therefore elicit their effect by a different mechanism.

The present invention provides a compound of formula I, or a salt or prodrug thereof:

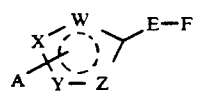
(I)

wherein the broken circle represents two non-adjacent double bonds in any position in the five-membered ring;

W, X, Y and Z independently represent oxygen, sulphur, nitrogen or carbon, provided that one of W, X, Y and Z represents oxygen or sulphur and at least one of W, X, Y and Z represents carbon;

A represents hydrogen, hydrocarbon, halogen, cyano, trifluoromethyl, nitro, —OR$^x$, —OCOR$^x$, —ONR$^x$R$^y$, —SR$^x$, —NR$^x$R$^y$, —NR$^x$OR$^y$, —NR$^z$NR$^x$R$^y$, —NR$^x$COR$^y$, —NR$^x$CO$_2$R$^y$, —NR$^x$SO$_2$R$^y$, —NR$^z$CVNR$^x$R$^y$, —COR$^x$, —CO$_2$R$^x$ or —CONR$^x$R$^y$;

E represents a bond or a straight or branched alkylene chain containing from 1 to 4 carbon atoms;

F represents a group of formula

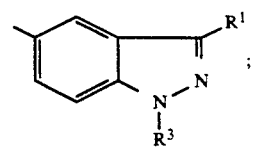

R$^1$ represents —CH$_2$.CHR$^4$.NR$^x$R$^y$ or a group of formula

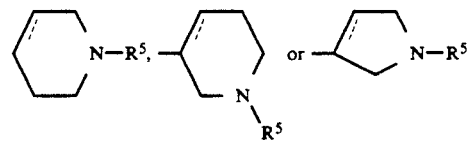

in which the broken line represents an optional chemical bond;

R$^3$, R$^4$ and R$^5$ independently represent hydrogen, C$_{1-6}$ alkyl, C$_{2-6}$ alkenyl or C$_{2-6}$ alkynyl;

R$^x$ and R$^y$ independently represent hydrogen or hydrocarbon, or R$^x$ and R$^y$ together represent a C$_{2-6}$ alkylene group;

R$^z$ represents hydrogen or hydrocarbon;

V represents oxygen, sulphur or a group of formula =N.G; and

G represents hydrocarbon or an electron-withdrawing group.

For use in medicine, the salts of the compounds of formula I will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable non-toxic acid such as hydrochloric acid, fumaric acid, maleic acid, succinic acid, acetic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups, including heterocyclic groups, containing up to 18 carbon atoms, suitably up to 15 carbon atoms, and conveniently up to 12 carbon atoms. Suitable hydrocarbon groups include C$_{1-6}$ alkyl, C$_{2-6}$ alkenyl, C$_{2-6}$ alkynyl, C$_{3-7}$ cycloalkyl, C$_{3-7}$ cycloalkyl (C$_{1-6}$) alkyl, aryl, aryl (C$_{1-6}$) alkyl, C$_{3-7}$ heterocycloalkyl, C$_{3-7}$ heterocycloalkyl (C$_{1-6}$) alkyl, heteroaryl and heteroaryl (C$_{1-6}$) alkyl.

Suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl and t-butyl.

Suitable alkenyl groups include straight-chained and branched alkenyl groups containing from 2 to 6 carbon atoms. Typical examples include vinyl and allyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Suitable aryl groups include phenyl and naphthyl groups.

Particular aryl($C_{1-6}$)alkyl groups include benzyl, phenethyl and phenylpropyl.

Suitable heterocycloalkyl groups include azetidinyl, pyrrolidyl, piperidyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, dibenzofuryl, thienyl, benzthienyl, imidazolyl, oxadiazolyl and thiadiazolyl groups.

A particular heteroaryl ($C_{1-6}$)alkyl group is pyridylmethyl.

The hydrocarbon group may in turn be optionally substituted by one or more groups selected from $C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-6}$ alkylenedioxy, nitro, cyano, carboxy, $C_{2-6}$ alkoxycarbonyl, $C_{2-6}$ alkoxycarbonyl($C_{1-6}$alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, —$NR^vR^w$, —$NR^vCOR^w$, —$NR^vCO_2R^w$, —$NR^vSO_2R^w$, —$CH_2NR^vSO_2R^w$, —$NHCONR^vR^w$, —$CONR^vR^w$, —$SO_2NR^vR^w$ and —$CH_2SO_2NR^vR^w$, in which $R^v$ and $R^w$ independently represent hydrogen, $C_{1-6}$ alkyl, aryl or aryl($C_{1-6}$)alkyl, or $R^v$ and $R^w$ together represent a $C_{2-6}$ alkylene group.

When $R^x$ and $R^y$, or $R^v$ and $R^w$, together represent a $C_{2-6}$ alkylene group, this group may be an ethylene, propylene, butylene, pentamethylene or hexamethylene group, preferably butylene or pentamethylene.

When the group G represents an electron-withdrawing group, this group is suitably cyano, nitro, —$COR^x$, —$CO_2R^x$ or —$SO_2R^x$, in which $R^x$ is as defined above.

The term "halogen" as used herein includes fluorine, chlorine, bromine and iodine, especially fluorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof are encompassed within the scope of the present invention.

The five-membered heteroaromatic ring in formula I containing the substituents W to Z may be, for example, a furan, thiophene, oxazole, thiazole, isoxazole, isothiazole, oxadiazole or thiadiazole ring, in particular a 1,2,4-oxadiazole, 1,3,4-oxadiazole, 1,2,4-thiadiazole, 1,3,4-thiadiazole, 1,3-oxazole or 1,3-thiazole ring. Preferably the ring is a 1,2,4-oxadiazole, 1,2,4-thiadiazole, 1,3-oxazole or 1,3-thiazole ring.

The alkylene chain E may be, for example, methylene, ethylene, 1-methylethylene, propylene or 2-methylpropylene. Alternatively, the group E may represent a single bond such that the indazole moiety F in formula I is attached directly to the five-membered heteroaromatic ring.

Suitable values for the group A include $C_{1-6}$ alkyl, $C_{3-7}$ cycloalkyl, aryl, aryl($C_{1-6}$)alkyl, $C_{3-7}$ heterocycloalkyl or heteroaryl($C_{1-6}$)alkyl, any of which groups may be optionally substituted; and hydrogen, halogen, cyano, trifluoromethyl, nitro, $C_{1-6}$ alkoxy, $C_{1-6}$ alkylthio, —$NR^xR^y$ or —$CONR^xR^y$, in which $R^x$ and $R^y$ are as defined above. Examples of optional substituents on the group A suitably include phenyl, trifluoromethyl, $C_{1-6}$ alkoxy, $C_{2-6}$ alkoxycarbonyl, $C_{2-6}$ alkylcarbonyl, $C_{1-6}$ alkylsulphonyl, arylsulphonyl, amino, mono- or di($C_{1-6}$)alkylamino, $C_{2-6}$ alkylcarbonylamino, arylcarbonylamino, $C_{2-6}$ alkoxycarbonylamino, $C_{1-6}$ alkylsulphonylamino, arylsulphonylamino, $C_{1-6}$ alkylsulphonylaminomethyl, aminocarbonylamino, mono- or di($C_{1-6}$)alkylaminocarbonylamino, mono- or diarylaminocarbonylamino, pyrrolidylcarbonylamino, aminocarbonyl, mono- or di($C_{1-6}$)alkylaminocarbonyl, $C_{1-6}$ alkylaminosulphonyl, aminosulphonylmethyl, and mono- or di($C_{1-6}$)alkylaminosulphonylmethyl.

Particular values of A include methyl, methoxymethyl, aminomethyl, dimethylaminomethyl, acetylaminomethyl, benzoylaminomethyl, t-butoxycarbonylaminomethyl, methylsulphonylaminomethyl, phenylsulphonylaminomethyl, aminocarbonylmethyl, ethyl, aminoethyl, acetylaminoethyl, benzoylaminoethyl, methoxycarbonylaminoethyl, ethoxycarbonylaminoethyl, t-butoxycarbonylaminoethyl, methylsulphonylaminoethyl, aminocarbonylaminoethyl, methylaminocarbonylaminoethyl, t-butylaminocarbonylaminoethyl, phenylaminocarbonylaminoethyl, pyrrolidylcarbonylaminoethyl, cyclopropyl, phenyl, methylsulphonylaminophenyl, aminocarbonylphenyl, methylaminocarbonylphenyl, methylsulphonylaminomethylphenyl, aminosulphonylmethylphenyl, methylaminosulphonylmethylphenyl, dimethylaminosulphonylmethylphenyl, naphthyl, benzyl, diphenylmethyl, trifluoromethylbenzyl, methoxybenzyl, acetylaminobenzyl, methylsulphonylaminobenzyl, aminocarbonylaminobenzyl, aminocarbonylbenzyl, methylaminocarbonylbenzyl, methylsulphonylbenzyl, methylaminosulphonylbenzyl, phenethyl, phenylpropyl, acetylpiperazinyl, methoxycarbonylpiperazinyl, t-butoxycarbonylpiperazinyl, methylaminocarbonylpiperazinyl, methylsulphonylpiperazinyl, phenylsulphonylpiperazinyl, pyridylmethyl, methoxypyridylmethyl, amino, methylamino, benzylamino, dimethylamino, t-butoxycarbonylaminoethylamino, methylsulphonylaminoethylamino, aminocarbonyl, methylaminocarbonyl, azetidinylcarbonyl and pyrrolidylcarbonyl.

Representative values of $R^1$ include aminoethyl, N-methylaminoethyl, N,N-dimethylaminoethyl and 1-methyl-4-piperidyl. Preferably, $R^1$ represents aminoethyl or N,N-dimethylaminoethyl.

Suitably, the groups $R^3$ to $R^5$ independently represent hydrogen or $C_{1-6}$ alkyl, in particular hydrogen or methyl.

A particular sub-class of compounds according to the invention is represented by the compounds of formula IIA, and salts and prodrugs thereof:

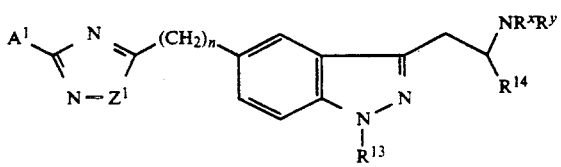

(IIA)

wherein
Z¹ represents oxygen or sulphur;
n is zero, 1, 2 or 3;
A¹ represents $C_{1-6}$ alkyl, $C_{2-6}$ alkenyl, $C_{2-6}$ alkynyl, $C_{3-7}$ cycloalkyl, aryl, aryl ($C_{1-6}$)alkyl, $C_{3-7}$ heterocycloalkyl, heteroaryl or heteroaryl ($C_{1-6}$)alkyl, any of which groups may be optionally substituted; or hydrogen, halogen, cyano, trifluoromethyl, nitro, $C_{1-6}$ alkoxy, $C_{1-6}$ alkylthio, —NR$^x$R$^y$ or —CONR$^x$R$^y$;
R¹³ and R¹⁴ independently represent hydrogen, $C_{1-6}$ alkyl, $C_{2-6}$ alkenyl or $C_{2-6}$ alkynyl; and
R$^x$ and R$^y$ independently represent hydrogen or hydrocarbon, or R$^x$ and R$^y$ together represent a $C_{2-6}$ alkylene group.

Examples of optional substituents on the group A¹ suitably include phenyl, trifluoromethyl, $C_{1-6}$ alkoxy, $C_{2-6}$ alkoxycarbonyl, $C_{2-6}$ alkylcarbonyl, $C_{1-6}$ alkylsulphonyl, arylsulphonyl, amino, mono- or di($C_{1-6}$)alkylamino, $C_{2-6}$ alkylcarbonylamino, arylcarbonylamino, $C_{2-6}$ alkoxycarbonylamino, $C_{1-6}$ alkylsulphonylamino, arylsulphonylamino, $C_{1-6}$ alkylsulphonylaminomethyl, aminocarbonylamino, mono- or di($C_{1-6}$)alkylaminocarbonylamino, mono- or diarylaminocarbonylamino, pyrrolidylcarbonylamino, aminocarbonyl, mono- or di($C_{1-6}$)alkylaminocarbonyl, $C_{1-6}$ alkylaminosulphonyl, aminosulphonylmethyl, and mono- or di($C_{1-6}$)alkylaminosulphonylmethyl.

Particular values of A¹ with respect to formula IIA include methyl, methoxymethyl, aminomethyl, dimethylaminomethyl, acetylaminomethyl, benzoylaminomethyl, t-butoxycarbonylaminomethyl, methylsulphonylaminomethyl, phenylsulphonylaminomethyl, aminocarbonylmethyl, ethyl, aminoethyl, acetylaminoethyl, benzoylaminoethyl, methoxycarbonylaminoethyl, ethoxycarbonylaminoethyl, t-butoxycarbonylaminoethyl, methylsulphonylaminoethyl, aminocarbonylaminoethyl, methylaminocarbonylaminoethyl, t-butylaminocarbonylaminoethyl, phenylaminocarbonylaminoethyl, pyrrolidylcarbonylaminoethyl, cyclopropyl, phenyl, methylsulphonylaminophenyl, aminocarbonylphenyl, methylaminocarbonylphenyl, methylsulphonylaminomethylphenyl, aminosulphonylmethylphenyl, methylaminosulphonylmethylphenyl, dimethylaminosulphonylmethylphenyl, naphthyl, benzyl, diphenylmethyl, trifluoromethylbenzyl, methoxybenzyl, acetylaminobenzyl, methylsulphonylaminobenzyl, aminocarbonylaminobenzyl, aminocarbonylbenzyl, methylaminocarbonylbenzyl, methylsulphonylbenzyl, methylaminosulphonylbenzyl, phenethyl, phenylpropyl, acetylpiperazinyl, methoxycarbonylpiperazinyl, t-butoxycarbonylpiperazinyl, methylaminocarbonylpiperazinyl, methylsulphonylpiperazinyl, phenylsulphonylpiperazinyl, pyridylmethyl, methoxypyridylmethyl, amino, methylamino, benzylamino, dimethylamino, t-butoxycarbonylaminoethylamino, methylsulphonylaminoethylamino, aminocarbonyl, methylaminocarbonyl, azetidinylcarbonyl and pyrrolidylcarbonyl. In a preferred embodiment, A¹ represents amino.

Preferably, R¹³ and R¹⁴ each represents hydrogen. Preferred values of R$^x$ and R$^y$ with respect to formula IIA include hydrogen and methyl.

Another sub-class of compounds according to the invention is represented by the compounds of formula IIB, and salts and prodrugs thereof:

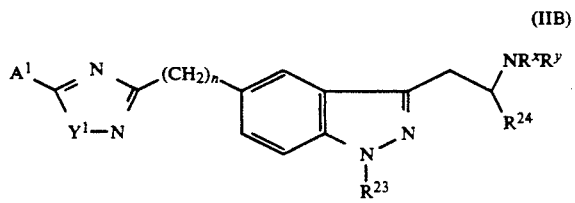

(IIB)

wherein
Y¹ represents oxygen or sulphur;
n is zero, 1, 2 or 3;
A¹ is as defined with reference to formula IIA above;
R²³ and R²⁴ independently represent hydrogen, $C_{1-6}$ alkyl, $C_{2-6}$ alkenyl or $C_{2-6}$ alkynyl; and
R$^x$ and R$^y$ independently represent hydrogen or hydrocarbon, or R$^x$ and R$^y$ together represent a $C_{2-6}$ alkylene group.

Particular values of A¹ with respect to formula IIB include methyl and benzyl. Preferably, R²³ and R²⁴ each represents hydrogen. Preferred values of R$^x$ and R$^y$ with respect to formula IIB include hydrogen and methyl.

A further sub-class of compounds according to the invention is represented by the compounds of formula IIC, and salts and prodrugs thereof:

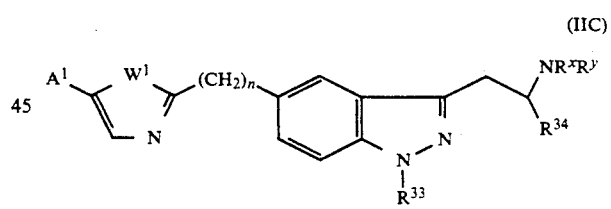

(IIC)

wherein
W¹ represents oxygen or sulphur;
n is zero, 1, 2 or 3;
A¹ is as defined with reference to formula IIA above;
R³³ and R³⁴ independently represent hydrogen, $C_{1-6}$ alkyl, $C_{2-6}$ alkenyl or $C_{2-6}$ alkynyl; and
R$^x$ and R$^y$ independently represent hydrogen or hydrocarbon, or R$^x$ and R$^y$ together represent a $C_{2-6}$ alkylene group.

A particular value of A¹ with respect to formula IIC is methyl. Preferably, R³³ and R³⁴ each represents hydrogen. Preferred values of R$^x$ and R$^y$ with respect to formula IIC include hydrogen and methyl.

A still further sub-class of compounds according to the invention is represented by the compounds of formula IID, and salts and prodrugs thereof:

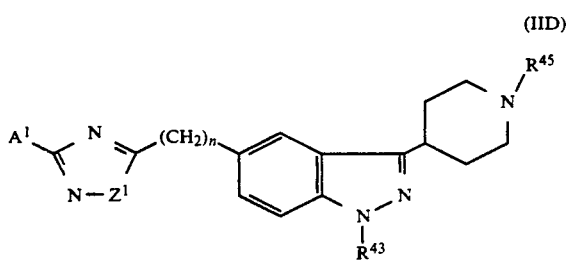 (IID)

wherein $Z^1$ represents oxygen or sulphur;

n is zero, 1, 2 or 3;

$A^1$ is as defined with reference to formula IIA above;

$R^{43}$ and $R^{45}$ independently represent hydrogen, $C_{1-6}$ alkyl, $C_{2-6}$ alkenyl or $C_{2-6}$ alkynyl; and $R^x$ and $R^y$ independently represent hydrogen or hydrocarbon, or $R^x$ and $R^y$ together represent a $C_{2-6}$ alkylene group.

Particular values of $A^1$ with respect to formula IID include amino, and optionally substituted benzyl or pyridylmethyl, especially methylsulphonylaminobenzyl.

Preferably, $R^{43}$ represents hydrogen. Preferably, $R^{45}$ represents hydrogen or $C_{1-6}$ alkyl, especially methyl.

Specific compounds within the scope of the present invention include:

2-[5-(3-methyl-1,2,4-oxadiazol-5-yl)-1H-indazol-3-yl]ethylamine;

N,N-dimethyl-2-[5-(3-methyl-1,2,4-oxadiazol-5-yl)-1H-indazol-3-yl]ethylamine;

N,N-dimethyl-2-[5-(3-amino-1,2,4-thiadiazol-5-yl)-1H-indazol-3-yl]ethylamine;

and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, or suppositories, for oral, parenteral or rectal administration. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The oxadiazole compounds of this invention may be prepared by a process which comprises reacting a reactive derivative of a carboxylic acid of formula $R^c$—$CO_2H$ with a compound either of formula III or of formula IV, or a salt thereof:

 (III)

 (IV)

wherein one of $R^c$ and $R^d$ is a group of formula A, and the other is a group of formula —E—F, as defined with reference to formula I above.

Suitable reactive derivatives of the acid $R^c$—$CO_2H$ include esters, for example $C_{1-4}$ alkyl esters; thioesters, for example pyridylthioesters; acid anhydrides, for example $(R^cCO)_2O$; acid halides, for example acid chlorides; orthoesters; and primary, secondary and tertiary amides.

A preferred reactive derivative of the acid $R^c$—$CO_2H$ is the iminoether derivative of formula V:

 (V)

where R is $C_{1-4}$ alkyl.

When the compound of formula III is employed the product of the reaction is a 1,2,4-oxadiazole. It will be appreciated that the compound III can also be considered as the alternative tautomeric form IIIA:

 (IIIA)

wherein $R^d$ is as defined above.

A 3-substituted-1,2,4-oxadiazol-5-yl compound is produced if $R^c$ represents a group —E—F and $R^d$ in formula III represents a group A; whereas a 5-substituted-1,2,4-oxadiazol-3-yl compound is produced by the process of this invention when $R^c$ represents a group A and $R^d$ represents a group —E—F. A preferred reactive derivative of the acid $R^c$—$CO_2H$ in this case is a $C_{1-4}$ alkyl ester. The reaction is conveniently carried out in the presence of a strong base, e.g. sodium hydride, using a suitable solvent, for example tetrahydrofuran, dimethylformamide or a lower alkanol such as ethanol, propanol or isopropanol, at about 20° C. to 100° C. for about 1 to 6 hours.

When the compound of formula IV is employed, the product of the process of this invention is a 1,3,4-oxadiazole. In this case, a preferred reactive derivative of the acid $R^c$—$CO_2H$ is an orthoester of formula $R^cC(OR^p)_3$ where $R^p$ represents $C_{1-3}$ alkyl. The process is conveniently effected by heating the hydrazide IV with the orthoester in a solvent such as methanol at reflux temperature for about 2 to 8 hours. An intermediate of formula $R^d.CO.NH.N=C(R^c)OR^p$ may be isolated by evaporation of the solvent. The intermediate is then treated with a strong base such as potassium t-butoxide or 1,8-diazabicyclo[5.4.0]undec-7-ene, in butanol for about 10 to 24 hours at about 90° C. to 150° C.

The reactive derivative of a carboxylic acid of formula $R^c$—$CO_2H$ or the compound of formula III or IV, wherein $R^c$ or $R^d$ represents a group of formula —E—F, may be prepared by the cyclisation of a compound of formula VI:

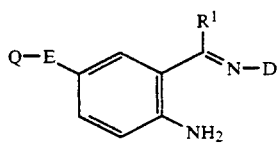
(VI)

wherein Q represents a reactive carboxylate moiety, or a group of formula —C(NOH)NH$_2$ or —CONHNH$_2$ or a protected derivative thereof or precursor thereto; E and $R^1$ are as defined above; and D represents a readily displaceable group; followed, where required, by N-alkylation by standard methods to introduce the moiety $R^3$.

The cyclisation of compound VI is conveniently achieved in a suitable organic solvent at an elevated temperature, for example in a mixture of m-xylene and 2,6-lutidine at a temperature in the region of 140° C.; or in the melt, which requires a temperature of approximately 170° C.

When the moiety Q in the compounds of formula VI represents a precursor to a group of formula —C(NOH)NH$_2$ or —CONHNH$_2$, this group is suitably a nitrile group.

The readily displaceable group D in the compounds of formula VI suitably represents a $C_{1-4}$ alkanoyloxy group, preferably acetoxy, or an arylsulphonyl group such as p-toluenesulphonyl (tosyl). Where D in the desired compound of formula VI represents acetoxy, this compound may be conveniently prepared by treating a carbonyl compound of formula VII:

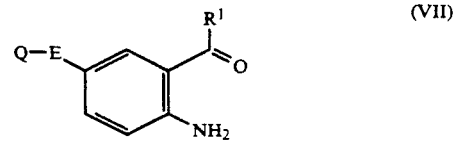
(VII)

wherein $R^1$, E and Q are as defined above; or a protected derivative thereof; with hydroxylamine hydrochloride, advantageously in pyridine at the reflux temperature of the solvent; followed by acetylation with acetic anhydride, advantageously in the presence of 4-dimethylaminopyridine, dimethylaminopyridine, in dichloromethane at room temperature.

The N-formyl protected derivative of the intermediate of formula VII may be conveniently prepared by ozonolysis of an indole derivative of formula VIII:

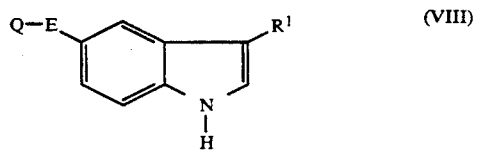
(VIII)

wherein $R^1$, E and Q are as defined above; followed by a reductive work-up, advantageously using dimethylsulphide.

The indole derivatives of formula VIII may be prepared by methods analogous to those described in the accompanying Examples, or by procedures well known from the art.

The 1,2,4-thiadiazoles of formula I may be prepared by a process which comprises the cyclisation of a compound of formula IX:

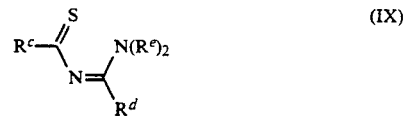
(IX)

wherein $R^c$ and $R^d$ are as defined above, and $R^e$ is hydrogen or an alkyl group.

Cyclisation of compound IX can be achieved using an aminating agent such as hydroxylamine-O-sulphonic acid in a lower alkanol such as methanol, ethanol or propanol, in the presence of pyridine, at between −20° C. and 50° C. for about 1-6 hours.

Cyclisation of compounds of formula IX in which $R^e$ is hydrogen may also be achieved by use of an oxidising agent such as bromine, iodine, hydrogen peroxide or nitric acid.

The compounds of formula IX above may be prepared by the processes described in *Comprehensive Heterocyclic Chemistry*, ed. A. R. Katritzky and C. W. Rees, Pergamon Press, 1984, Vol. 6, p. 496, or by methods analogous thereto.

The 1,2,4-thiadiazoles may also be prepared by cycloaddition of a nitrile sulphide $R^c$—C≡N$^+$—S$^-$ with a nitrile of formula $R^d$—CN where $R^c$ and $R^d$ are as defined above.

1,3,4-Thiadiazoles of this invention may be prepared by dehydration of a thiosemicarbazide of formula $R^cCSNHNHCONR^sR^t$, where $R^c$ is as defined above and $R^s$ and $R^t$ are hydrogen or an alkyl group, with a dehydrating agent such as sulphuric acid, polyphosphoric acid or methanesulphonic acid; followed by attachment of the R$^d$ group by conventional means.

1,2,5-Thiadiazoles of this invention may be prepared by reacting a diamine of the type

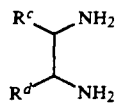

where R$^c$ and R$^d$ are as defined above, with a sulphur chloride such as thionyl chloride or sulphur dichloride.

The oxazoles and thiazoles of this invention may be prepared by reaction of an amide or thioamide of formula X with a α-haloketone of formula XI:

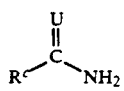

(X)

(XI)

wherein U is oxygen or sulphur, Hal represents halogen, and R$^c$ and R$^d$ are as defined above. The conditions for this reaction are as described in *Synthesis*, 1975, 389.

Furans possessing a 2,5-substitution pattern may, for example, be prepared by treating a compound of formula XII:

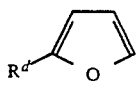

(XII)

wherein R$^d$ is a previously defined; with a reagent capable of generating an anion thereof by abstraction of the proton adjacent to the oxygen atom; and subsequently reacting the anionic species thereby obtained with an electrophilic species capable of providing the moiety R$^c$, wherein R$^c$ is as previously defined.

The reagent capable of generating an anion of the compound of formula XII by abstraction of the proton adjacent to the oxygen atom is suitably an alkyl lithium, e.g. n-butyllithium.

The electrophilic species capable of providing the moiety R$^c$ is suitably a carbonyl-containing compound or a compound of formula R$^c$—L, in which L represents a suitable leaving group such as halogen atom, e.g. chlorine or bromine. In the former case, the compound obtained from reaction of the carbonyl compound with the anion derived from compound XII will contain a hydroxy moiety as part of the resulting R$^c$ group. This hydroxy moiety may, if desired, be retained intact, or may be removed by standard procedures, for example elimination with POCl$_3$ followed by hydrogenation.

Illustrative experimental details for performing the above process are, for example, described in *J. Med. Chem.*, 1990, 33, 1128.

The intermediate of formula XII may be prepared by conventional methods, for example:

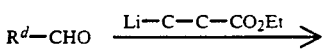

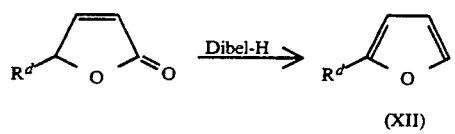

(XII)

wherein R$^d$ is as defined above.

In an alternative process, the compounds according to the invention may be prepared by a method which comprises reacting a compound of formula XIII:

(XIII)

with a reagent which provides an anion $^-$R$^c$, where W, X, Y, Z, R$^c$ and R$^d$ are as previously defined and Hal represents halogen.

Compound XIII may be prepared by conventional procedures known from the art. For example, if compound XIII is a 1,2,4-thiadiazole, this compound may be prepared by the general method described in *Chem. Ber.*, 1957, 90, 182.

Reagents which may provide the anion $^-$R$^c$ include Grignard reagents R$^c$MgHal (where Hal=halogen); organocuprate reagents such as LiR$^c$$_2$Cu; organolithium reagents R$^c$Li; or compounds which stabilise the anion by means of an adjacent activating group such as an ester or enolisable ketone function. In this case, the adjacent ester or ketone function may be retained after the process is complete, or may be removed. For example, an ester moiety may be hydrolysed and decarboxylated.

In a further process, the compounds according to the invention may be prepared by a method which comprises cyclising a compound of formula XIV:

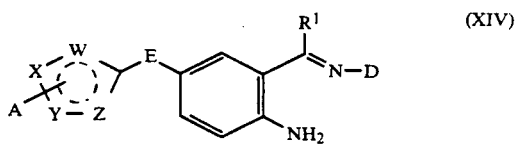

(XIV)

wherein W, X, Y, Z, A, E, R$^1$ and D are as defined above; followed; where required, by N-alkylation by standard methods to introduce the moiety R$^3$.

As with the cyclisation of compound VI, that of compound XIV is conveniently achieved in a suitable organic solvent at an elevated temperature, for example in a mixture of m-xylene and 2,6-lutidine at a temperature in the region of 140° C.; or in the melt.

The compounds of formula XIV may, for example, be prepared from the corresponding compound of formula XV:

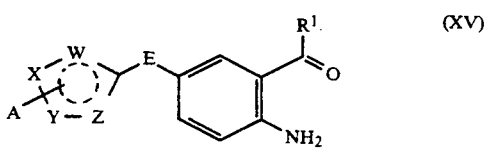

(XV)

wherein W, X, Y, Z, A, E and R$^1$ are as defined above; or a protected derivative thereof; which in turn may be prepared from the corresponding compound of formula XVI:

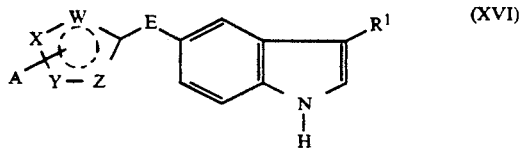

wherein W, X, Y, Z, A, E and $R^1$ are as defined above; using methods analogous to those described above with reference to the compounds of formulae VII and VIII. Thus, for example, when Q in the compounds of formula VIII represents a group of formula —C(NOH)NH$_2$ or —CONHNH$_2$, the compounds of formula XVI may be prepared therefrom by reaction with a reactive derivative of a carboxylic acid of formula A—CO$_2$H, where A is as defined previously. Alternatively, when Q in the compounds of formula VIII represents a reactive carboxylate moiety, the compounds of formula XVI may be prepared therefrom by reaction with a compound of formula A—C(NOH)NH$_2$ or A—CONHNH$_2$.

The compounds of formula Q—E—F, wherein Q, E and F are as defined above, and salts and prodrugs thereof, are novel compounds in their own right, and accordingly represent a further feature of the present invention. A particular subgroup of such compounds is represented by the compounds of formula $Q^1$—E—F, wherein E and F are as defined above and $Q^1$ represents a $C_{1-4}$ alkyl ester group; and salts and prodrugs thereof. Particularly preferred compounds in this context are 2-(5-ethoxycarbonyl-1H-indazol-3-yl)ethylamine; 2-(5-ethoxycarbonylmethyl-1H-indazol-3-yl)ethylamine;
2-(5-methoxycarbonylmethyl-1H-indazol-3-yl)ethylamine;
and salts and prodrugs thereof.

It will be appreciated that any compound of formula I initially obtained from any of the above processes may, where appropriate, subsequently be elaborated into a further compound of formula I by techniques known from the art. In particular, a compound of formula I wherein $R^3$ is hydrogen initially obtained may be converted into a compound of formula I wherein $R^3$ represents $C_{1-6}$ alkyl, $C_{2-6}$ alkenyl or $C_{2-6}$ alkynyl by standard techniques such as alkylation, for example by treatment with an alkyl iodide, e.g. methyl iodide, typically under basic conditions, e.g. sodium hydride in dimethylformamide. Similarly, a compound of formula I wherein $R^1$ represents a group of formula —CH$_2$.CHR$^4$.NH$_2$ initially obtained may be converted into a compound of formula I wherein $R^1$ represents a group of formula —CH$_2$.CHR$^4$.NR$^x$R$^y$ in which R$^x$ and R$^y$ are as defined above with the exception of hydrogen, for example by conventional N-alkylation or N-arylation techniques, e.g. by treatment with the appropriate aldehyde in the presence of a reducing agent such as sodium cyanoborohydride.

Where the above-described processes for the preparation of the compounds according to the invention give rise to mixtures of stereoisomers, these isomers may be separated by conventional techniques such as preparative chromatography.

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (—)-di-p-toluoyl-d-tartaric acid and/or (+)-di-p-toluoyl-l-tartaric acid followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene, *Protective Groups in Organic Synthesis*, John Wiley & Sons, 1981. The protecting groups may be removed at a convenient subsequent stage using methods known from the art.

The following Examples illustrate the preparation of compounds according to the invention.

The ability of test compounds to bind to 5-HT$_1$-like receptors was measured in membranes prepared from pig caudate using the procedure described in *J. Neurosci.*, 1987, 7, 894. Binding was determined using 2 nM 5-hydroxytryptamine creatinine sulphate, 5-[1,2-$^3$H(N)] as a radioligand. Cyanopindolol (100 nM) and measulergine (100 nM) were included in the assay to block out 5-HT$_{1A}$ and 5-HT$_{1C}$ binding sites respectively. The concentration of the compounds of the accompanying Examples required to displace 50% of the specific binding (IC$_{50}$) is below 1 μM in each case.

The activity of test compounds as agonists of the 5-HT$_1$-like receptor was measured in terms of their ability to mediate contraction of the saphenous vein of New Zealand White rabbits, using the procedure described in *Arch. Pharm.*, 1990, 342, 111. Agonist potencies were calculated as —log$_{10}$EC$_{50}$ (pEC$_{50}$) values, from plots of percentage 5-HT (1 μm) response against the concentration of the agonist. The compound of accompanying Example 2 was tested and was found to possess a pEC$_{50}$ value in this assay of not less than 5.0.

EXAMPLE 1

2-(5-Carboethoxy-1H-indazol-3-yl)ethylamine hydrogen oxalate 1. 2-(5-Carboethoxy-1H-indol-3-yl)ethylamine a. Ethyl-p-hydrazinobenzoate hydrochloride A solution of sodium nitrite (17.0 g, 0.24 mol) in water (90 ml) was added to a cooled solution of ethyl-p-amino benzoate (40 g, 0.24 mol) in concentrated hydrochloric acid (225 ml) at such a rate that the temperature did not exceed 0° C. The mixture was stirred at 0° C. for 10 minutes before adding a stirred solution of tin (II) chloride dihydrate (202 g, 0.89 mol) in concentrated hydrochloric acid (135 ml) at such a rate that the temperature did not exceed —5° C. The resulting suspension was allowed to warm to room temperature over a 1 hour period, filtered and washed with ether. m.p. 215°–217° C. NMR δ (360 MHz, D$_2$O) 1.38 (3H, t, J=7 Hz), 4.37 (2H, q, J=7 Hz), 7.06 (2H, d, J=9 Hz), 8.03 (2H, d, J=9 Hz).

b. 2-(5-Carboethoxy-1H-indol-3-yl)ethylamine

A solution of ethyl-p-hydrazinobenzoate hydrochloride (10 g, 46 mmol) and 4-chlorobutanal dimethyl acetal (7.8 g, 46 mmol) in ethanol/water (5:1, 500 ml) was heated at reflux for 2 hours. The solvent was removed under vacuum and the residue chromatographed through silica gel eluting with dichloromethane/ethanol/ammonia (40:8:1) to give the title indole (3.69 g) as an oil. NMR δ (360 MHz, CDCl$_3$) 1.42 (3H, t, J=7 Hz), 2.94 (2H, t, J=7 Hz), 3.06 (2H, t, J=7 Hz), 4.40 (2H, q, J=7 Hz), 7.10 (1H, br s), 7.35 (1H, d, J=9 Hz), 7.91 (1H, dd, J=9 and 2 Hz), 8.30 (1H, br s), 8.38 (1H, s).

2. N-(tert-Butyloxycarbonyl)-2-(5-carboethoxy-1H-indol-3-yl)ethylamine

To a stirred solution of 2-(5-carboethoxy-1H-indol-3-yl)ethylamine hydrochloride (2.0 g, 7.4 mmol) and di-tert-butyldicarbonate (2.06 g, 9.4 mmol) in dichloromethane (52 ml) at 0° C., was added triethylamine (1.3 ml, 9.4 mmol). The solution was stirred overnight at room temperature, then partitioned with water (50 ml). The organic layer was separated, dried (MgSO$_4$) and evaporated in vacuo. The crude residue was chromatographed using 95:5 dichloromethane:methanol, to give N-(tert-butyloxycarbonyl)-2-(5-carboethoxy-1H-indol-3-yl)ethylamine (1.58 g, 64%) as an oil. NMR δ (250 MHz, CDCl$_3$) 1.44 (12H, m), 2.88 (2H, t, J=7 Hz), 3.49 (2H, m), 4.41 (2H, q, J=7 Hz), 4.61 (1H, br s), 7.09 (1H, d, J=2 Hz), 7.37 (1H, d, J=9 Hz), 7.92 (1H, dd, J=9 and 2 Hz), 8.35 (2H, m).

3. Ethyl-4-formylamino-3-[3′-(N-tert-butyloxycarbonylamino)propionyl]benzoate Ozone was bubbled through a solution of N-(tert-butyloxycarbonyl)-2(5-carboethoxy-1H-indol-3-yl)ethylamine (6.06 g, 18 mmol) in dichloromethane (300 ml) at −78° C. for 2 hours. Dimethyl sulphide (8 ml, 110 mmol) was then added dropwise at −78° C., and the solution allowed to attain room temperature. After stirring at room temperature overnight the solvents were evaporated in vacuo. Ether (100 ml) was added and the desired product (4.5 g, 92%) was collected by filtration. m.p. 135°–137° C. NMR δ (250 MHz, CDCl$_3$) 1.43 (12H, m) 3.32 (2H, t, J=6Hz), 3.66 (2H, m), 4.42 (2H, q, J=7 Hz), 5.05 (1H, br s), 8.27 (1H, dd, J=9 and 2 Hz), 8.56 (1H, br s), 8.60 (1H, d, J=2 Hz), 8.84 (1H, br s), 11.66 (1H, br s).

4. Ethyl-4-amino-3-[3′-(N-tert-butyloxycarbonylamino)-1-hydroxyiminopropyl]benzoate A solution of ethyl-4-formylamino-3-[3′-(N-tert-butyloxycarbonylamino)propionyl]benzoate (7.04 g, 20 mmol) and hydroxylamine hydrochloride (7.65 g, 110 mmol) in pyridine (200 ml), was heated at reflux for 15 hours. After this time the solution was cooled to ambient temperature and the solvent evaporated in vacuo. The residue was chromatographed (eluent 1:1 petrol:ethyl acetate) to give the title oxime (5.0 g, 71%) as a solid. m.p. 138°–140° C. NMR δ (250 MHz, CDCl$_3$) 1.40 (12H, m), 3.13 (2H, t, J=7 Hz), 3.40 (2H, m), 4.31 (2H, q, J=7 Hz), 5.19 (1H, br s), 6.11 (2H, br s), 6.66 (1H, d, J=9 Hz), 7.73 (1H, dd, J=9 and 2 Hz), 8.10 (1H, br s), 10.46 (1H, br s).

5. Ethyl-4-amino-3-[3′-(N-tert-butyloxycarbonylamino)-1′-acetoxyiminopropyl]benzoate To a stirred solution of ethyl-4-amino-3-[3′-(N-tert-butyloxycarbonylamino)-1′-hydroxyiminopropyl]benzoate (4.8 g, 14 mmol) and dimethylamino pyridine (1.67 g, 14 mmol) in dichloromethane (200 ml) was added acetic anhydride (1.3 ml, 14 mmol), under an atmosphere of nitrogen. After 2 hours the solution was poured into water (200 ml) and partitioned. The organic layer was separated, washed once more with water (200 ml), then the combined organic phases dried (MgSO$_4$). The solvent was removed in vacuo, to afford an oily solid. Ether (200 ml) was added, and the mixture evaporated in vacuo once more to give a white solid. The solid was taken up in more ether (100 ml) and filtered off, to afford the title compound (4.4 g, 82%) as a white solid. m.p. 130°–135° C. NMR δ (250 MHz, CDCl$_3$) 1.40 (12H, m), 2.27 (3H, s), 3.18 (2H, t, J=7 Hz), 3.43 (2H, m), 4.33 (2H, q, J=7 Hz), 4.70 (1H, br s), 6.69 (1H, d, J=9 Hz), 7.82 (1H, dd, J=9 and 2 Hz), 8.17 (1H, br s).

6. N-(tert-Butyloxycarbonyl)-2-(5-carboethoxy-1H-indazol-3-yl)ethylamine

A solution of ethyl-4-amino-3-[3′-(N-tert-butyloxycarbonylamino)-1′-acetoxyiminopropyl]benzoate (2.8 g, 7.1 mmol) and 2,6-lutidine (0.83 ml, 7.1 mmol) in m-xylene (200 ml), was heated at reflux in Dean-Stark apparatus for 5 hours. The solution was then cooled to ambient temperature and the solvent evaporated in vacuo. The crude residue was purified by flash chromatography (eluent 1:1 petrol:ethyl acetate) to give the indazole (0.95 g, 67%) as a colourless oil. NMR (250 MHz, CDCl$_3$) δ 1.42 (12H, m), 3.20 (2H, t, J=7 Hz), 3.65 (2H, m), 4.41 (2H, q, J=7 Hz), 5.09 (1H, br t), 7.44 (1H, d, J=9 Hz), 8.05 (1H, dd, J=9 and 2 Hz), 8.45 (1H, br s), 10.50 (1H, br s).

7. 2-(5-Carboethoxy-1H-indazol-3-yl)ethylamine hydrogen oxalate

A solution of N-(tert-butyloxycarbonyl)-2-(5-carboethoxy-1H-indazol-3-yl)ethylamine (461 mg, 1.4 mmol) and trifluoroacetic acid (1.5 ml) in dichloromethane (20 ml), under an atmosphere of nitrogen, was stirred for 4 hours. The mixture was then evaporated and the crude residue chromatographed using a gradient elution (1:1 petrol:ethyl acetate then 30:8:1 dichloromethane:ethanol:ammonia). This afforded 2-(5-carboethoxy-1H-indazol-3-yl)ethylamine (218 mg, 67%) as a pale yellow solid. The oxalate salt was prepared: M.p. 212°–214° C. NMR (360 MHz, D$_2$O-D$_6$-DMSO) δ 1.41 (3H, t, J=7 Hz), 3.39 (2H, m), 3.50 (2H, m), 4.40 (2H, q, J=7 Hz), 7.61 (1H, d, J=9 Hz), 8.02 (1H, dd, J=9 and 2 Hz), 8.50 (1H, br s). m/z (CI, NH$_3$), 234 (M+1), 204, 186, 151, 131, 91.

EXAMPLE 2

2-[5-(3-Methyl-1,2,4-oxadiazol-5-yl)-1H-indazol-3-yl])ethylamine hydrogen oxalate To a stirred solution of ethanol (10 ml), under an atmosphere of nitrogen, was added sodium (64 mg, 2.8 mmol) cautiously. After dissolution methyl acetamide oxime (228 mg, 3.1 mmol) was added portionwise and the mixture stirred at room temperature for 30 minutes. After this time a solution of 2-(5-carboethoxy-1H- indazol-3-yl)ethylamine (218 mg, 0.93 mmol) in ethanol (5 ml) was added, and the reaction heated at reflux for 10 hours. The solution was then cooled to ambient temperature and the solvent evaporated in vacuo. The crude residue was chromatographed, using dichloromethane:ethanol:ammonia (35:8:1) as the eluent, to give a mixture of the desired product and starting material in an 80:20 ratio. Therefore, both compounds were combined and the reaction repeated using a further 52 mg of the oxime and 15 mg of sodium in ethanol (15 ml). After heating the mixture at reflux for a further 9 hours, the mixture was cooled to room temperature, evaporated in vacuo, and chromatographed (eluent dichloromethane:ethanol:ammonia 35:8:1). 2-[5-(3-Methyl-1,2,4-oxadiazol-5-yl)-1H-indazol-3-yl]ethylamine (63 mg, 28%) was isolated as a colourless oil. The oxalate salt was prepared: M.p. 230°-233° C. NMR (360 MHz, $D_2O$-$D_6$-DMSO) δ 2.40 (3H, s), 3.38 (2H, t, J=7 Hz), 3.46 (2H, t, J=7 Hz), 7.66 (1H, d, J=9 Hz), 7.93 (1H, d, J=9 Hz), 8.39 (1H, s). m/z (Cl, $NH_3$), 244 (M+1), 212, 166, 151, 130.

EXAMPLE 3

N,N-Dimethyl-2-[5-(3-methyl-1,2,4-oxadiazol-5-yl)-1H-indazol-3-yl]ethylamine hydrogen oxalate A solution of formaldehyde (0.75 ml of a 37% (w/v) solution in water, 9.3 mmol) in methanol (5 ml) was added dropwise, under a nitrogen atmosphere, to a stirred solution of 2-(5-carboethoxy-1H-indazol-3-yl)ethylamine (541 mg, 2.32 mmol), sodium cyanoborohydride (0.29 g, 4.64 mmol) and acetic acid (0.42 ml, 7.0 mmol) in methanol (11 ml). After 3 hours the methanol was evaporated in vacuo and the residue diluted with dichloromethane (30 ml). The solution was washed with saturated potassium carbonate solution (30 ml), and the organic phase separated. The aqueous layer was extracted with more dichloromethane (2×30 ml), then the organic phases combined, dried ($MgSO_4$) and evaporated in vacuo. The crude residue was chromatographed, using dichloromethane:ethanol:ammonia 80:8:1 as the eluent. Two inseparable products (Rf 0.4) were collected, one of which was the desired N,N-dimethyl-2-(5-carboethoxy-1H-indazol-3-yl)ethylamine. This was not purified further.

To a stirred solution of ethanol (5 ml), under an atmosphere of nitrogen, was added sodium (63 mg, 2.75 mmol) cautiously. After dissolution, methyl acetamide oxime (204 mg, 2.75 mmol) was added portionwise and the mixture stirred at room temperature for 30 minutes. After this time a solution of the above mixture (120 mg) (Rf 0.4 in dichloromethane:ethanol:ammonia 80:8:1) in ethanol (5 ml) was added, and the solution heated at reflux for 20 hours. The mixture was then cooled to ambient temperature and the solvent removed in vacuo. Dichloromethane (20 ml) was added and the solution partitioned with water (20 ml). The organic layer was separated and the aqueous phase extracted with more dichloromethane (2×20 ml). The organic layers were combined, dried ($MgSO_4$) and evaporated in vacuo. The crude residue was chromatographed (eluent dichloromethane:ethanol:ammonia 50:8:1) to afford N,N-dimethyl-2-[5-(3-methyl-1,2,4-oxadiazol-5-yl)-1H-indazol-3-yl]ethylamine (66 mgs) as a colourless oil. The oxalate salt was prepared: m.p. 207°-210° C. NMR (360 MHz, $D_2O$) δ 2.34 (3H, s), 3.00 (6H, s), 3.42 (2H, t, J=7 Hz), 3.64 (2H, t, J=7 Hz), 7.55 (1H, d, J=9 Hz), 7.76 (1H, dd, J=9 and 1 Hz), 8.14 (1H, s). m/z (CI, $NH_3$), 272 (M+1), 186.

EXAMPLE 4

N,N-Dimethyl-2-(5-carbomethoxymethyl-1H-indazol-3-yl)ethylamine

1.4-(Carboethoxymethyl)phenylhydrazine. Hydrochloride

The title compound was prepared from ethyl 4-aminophenylacetate by a similar method to that described for Example 1 (Step 1a); mp 171°-174° C. (absolute ethanol); $δ_H$ (360 MHz, DMSO-$d_6$) 10.02 (br s—$N^+H_3$), 8.14 (br s, —NH—), 7.16 (2H, d, J=8.5 Hz, Ar—H), 6.92 (2H, d, J=8.5 Hz, Ar—H), 4.06 (2H, q, J=7.1 Hz, —$OCH_2$—), 3.56 (2H, s, Ar—$CH_2$—), 1.17 (3H, t, J=7.1 Hz, —$CH_3$); m/z (EI) 194 (M+).

2.2-(5-Carboethoxymethyl-1H-indol-3-yl)ethylamine. Hydrochloride.

The title compound was prepared from 4-(carboethoxymethyl)phenylhydrazine hydrochloride and 4-chlorobutanal dimethylacetal by a similar method to that described for Example 1 (Step 1b); mp 204°-206° C. (ethanol/diethyl ether); $δ_H$ (360 MHz, DMSO-$d_6$) 10.70 (1H, br s, indole N-H), 8.09 (3H, br s, —$N^+H_3$), 7.43 (1H, s, Ar—H), 7.31 (1H, d, J=8.3 Hz, Ar—H), 7.23 (1H, d, J=2.3 Hz, Ar—H), 6.99 (1H, dd, J=8.3 and 1.6 Hz, Ar—H), 4.07 (2H, q, J=7.1 Hz, —$OCH_2$—), 3.68 (2H, s, Ar—$CH_2CO$—), 3.02 (4H, m, —$CH_2CH_2$—), 1.18 (3H, t, J=7.1 Hz, —$CH_3$); m/z (CI) 247 (M+ +1).

3.N-(tert.Butyloxycarbonyl)-2-(5-carboethoxymethyl-1H-indol-3-yl)ethylamine

The title compound was prepared in 98% yield from 2-(5-carboethoxymethyl-1H-indol-3-yl)ethylamine hydrochloride by a similar method to that described for Example 1 (Step 2); colourless thick oil; $δ_H$ (360 MHz, $CDCl_3$), 8.06 (1H, br s, indole N—H), 7.48 (1H, s, Ar—H), 7.30 (1H, d, J=8.3 Hz, Ar—H), 7.13 (1H, d, J=8.3 Hz, Ar—H), 6.99 (1H, s, Ar—H), 4.58 (1H, br s, —NH—), 4.15 (2H, q, J=7.1 Hz, —$OCH_2$—), 3.70 (2H, s, Ar—$CH_2$—CO—), 3.45 (2H, m, —$CH_2N$—), 2.92 (2H, t, J=6.8 Hz, —$CH_2$—), 1.43 (9H, s, t-Bu), 1.25 (3H, t, J=7.1 Hz, —$CH_3$); m/z (EI) 346 (M+).

4. Ethyl 4-formylamino-3-[3'-(N-tert-butyloxycarbonylamino)-propionyl]phenylacetate The title compound was prepared in 64% isolated yield from N-(tert-butyloxycarbonyl)-2-(5-carboethoxymethyl-1H-indol-3-yl)ethylamine by a similar method to that described for Example 1 (Step 3); pale yellow oil; $δ_H$ (360 MHz, $CDCl_3$) 11.49 (1H, br s), 8.75 (1H, d, J=7.5 Hz), 8.49 (1H, s), 7.63 (1H, s), 7.49 (1H, d, J=7.5 Hz), 5.02 (1H, br s), 4.17 (2H, q, J=7.1 Hz), 3.62 (2H, s), 3.53 (2H, br q, J=6 Hz), 3.28 (2H, br t, J=6 Hz), 1.43 (9H, s), 1.27 (3H, t, J=7.1 Hz); m/z (CI) 378 (M+).

5. Ethyl 4-amino-3-[3'-(N-tert-butyloxycarbonylamino)-1'-hydroxyiminopropyl]phenylacetate The title compound was prepared in 43% yield from the product of Step 4 using a similar method to that described for Example 1 (Step 4); off white solid; $δ_H$ (360 MHz, $CDCl_3$) 7.28 (1H, br s), 7.04 (1H, dd, J=8.2 and 1.8 Hz), 6.68 (1H, d, J=8.2 Hz), 4.93 (1H, br s), 4.14 (2H, q, J=7.1 Hz), 3.50 (2H, s), 3.40 (2H, m), 3.07 (2H, t, J=6.9 Hz), 1.42 (9H, s), 1.25 (3H, t, J=7.1 Hz); m/z (EI) 365 (M+).

6. Ethyl 4-amino-3-[3'-(N-tert-butyloxycarbonylamino)-1'-acetoxyiminopropyl]phenylacetate The title compound was prepared in 67% yield from ethyl 4-amino-3-[3'-(N-tert-butyloxycarbonylamino)-1'-hydroxyiminopropyl]phenylacetate by a similar method to that described for Example 1 (Step 5); pale yellow oil; $\delta_H$ (360 MHz, CDCl$_3$) 7.32 (1H, br s), 7.10 (1H, dd, J=8.3 and 1.9 Hz), 6.69 (1H, d, J=8.3 Hz), 4.77 (1H, br, s), 4.13 (2H, q, J=7.1 Hz), 3.51 (2H, s), 3.39 (2H, br q, 6.7 Hz), 3.11 (2H, t, J=6.7 Hz), 2.24 (3H, s), 1.42 (9H, s), 1.24 (3H, t, J=7.1 Hz); m/z (FAB) 408 (M+ +1).

7. N-(tert-Butyloxycarbonyl)-2-(5-carboethoxymethyl-1H-indazol-3-yl)ethylamine The title compound was prepared in 61% yield from ethyl 4-amino-3-[3'-(N-tert-butyloxycarbonylamino)-1'-acetoxyiminopropyl]phenylacetate as described for Example 1 (Step 6); $\delta_H$ (360 MHz, CDCl$_3$) 7.57 (1H, s), 7.39 (1H, d, J=8.4 Hz), 7.32 (1H, dd, J=8.4 and 1.5 Hz), 5.06 (1H, br s), 4.16 (2H, q, J=7.1 Hz), 3.72 (2H, s), 3.61 (2H, br q, J=6.5 Hz), 3.14 (2H, t, J=6.5 Hz), 1.43 (9H, s), 1.26 (3H, t, J=7.1 Hz); m/z (CI) 348 (M+ +1).

8. 2-(5-Carboethoxymethyl-1H-indazol-3-yl)ethylamine

The title compound was prepared in 80% yield from N-(tert-butyloxycarbonyl)-2-(5-carboethoxymethyl-1H-indazol-3-yl)ethylamine by a similar method to that described for Example 1 (Step 7); pale yellow solid; $\delta_H$ (360MHz, CDCl$_3$) 7.54 (1H, s), 736 (1H, d, J=8.5 Hz), 7.28 (1H, d, J=8.5 Hz), 4.16 (2H, q, J=7.1 Hz), 3.70 (2H, s), 3.24-3.02 (4H, m), 1.26 (3H, t, J=7.1 Hz); m/z (CI) 248 (M+ +1).

9. N,N-Dimethyl-2-(5-carbomethoxymethyl-1H-indazol-3-yl)ethylamine

To a cooled (0° C.) and stirred solution of 2-(5-carboethoxymethyl-1H-indazol-3-yl)ethylamine (0.42 g, 1.7 mmol) in absolute methanol (30 ml) and glacial acetic acid (0.48 ml, 8.5 mmol) was added sodium cyanoborohydride (0.21 g, 3.4 mmol) followed by dropwise addition of a solution of formaldehyde (38% w/v aqueous solution; 0.35 ml) in methanol (6 ml) over 8 minutes. The resulting solution was stirred at 0° C. for 20 minutes and at room temperature for 1.5 hours before saturated aqueous potassium carbonate (20 ml) was added and the methanol was removed under vacuum. The remaining aqueous solution was extracted with ethyl acetate (2×50 ml) and the combined organic phases were washed with brine (2×50 ml), dried (MgSO$_4$) and concentrated. Flash chromatography (silica gel, dichloromethane-methanol-ammonia 50:8:1) of the crude residue afforded 0.29 g (69%) of the title compound as a low-melting solid; $\delta_H$ (250 MHz, CDCl$_3$) 7.47 (1H, s), 7.16-7.07 (2H, m), 3.63 (2H, s), 3.62 (3H, s), 3.09 (2H, t, J=7.1 Hz), 2.74 (2H, t, J=7.1 Hz), 2.29 (6H, s); m/z (CI) 262 (M+ +1).

EXAMPLE 5

N,N-Dimethyl-2-[5-(3-amino-1,2,4-thiadiazol-5-yl)methyl-1H-indazol-3-yl]ethylamine. Oxalate

1. N,N-Dimethyl-2-[5-(4-methoxybenzyl)oxycarbonylmethyl-1H-indazol-3-yl]ethylamine To a cooled (−78° C.) and stirred solution of 4-methoxybenzyl alcohol (2 g, 14.5 mmol) in anhydrous tetrahydrofuran (30 ml) was added dropwise, under nitrogen, n-butyllithium (1.6M in hexane, 7.8 ml) over 10 minutes. After further 10 minutes at −78° C., a solution of N,N-dimethyl-2-(5-carbomethoxymethyl-1H-indazol-3-yl)ethylamine (780 mg, 3 mmol) in anhydrous tetrahydrofuran (20 ml) was added and the resulting solution was stirred at −78° C. for 1 hour and at room temperature for 2 hours. Solvents were removed under vacuum and the residue was azeotroped with toluene (2×30 ml). The remaining residue was diluted with water (50 ml) and extracted with diethyl ether (1×30 ml) and ethyl acetate (2×10 ml). The combined organic solutions were dried (MgSO$_4$) and concentrated. Flash chromatography of the remaining oil (silica gel, dichloromethane-methanol-ammonia 90:10:1) gave 958 mg (87%) of the title compound as an oil; $\delta_H$ (360 MHz, CDCl$_3$) 7.57 (1H, s), 7.36 (1H, d, J=8.5 Hz), 7.27 (3H, m), 6.86 (2H, m), 5.08 (2H, s), 3.80 (3H, s), 3.16 (2H, s), 3.16 (2H, m), 2.82 (2H, m), 2.36 (6H, s); m/z (CI) 368 (M+ +1).

2. N,N-Dimethyl-2-[5-(4-methoxybenzyl)oxycarbonylmethyl-1-tert-butyloxycarbonylindazol-3-yl]ethylamine To a stirred solution of the preceding ester (279 mg, 0.76 mmol) in anhydrous acetonitrile (5 ml) was added a solution of di-tert-butyl dicarbonate (200 mg, 0.92 mmol) in anhydrous acetonitrile (2 ml) followed by a solution of 4-dimethylaminopyridine (20 mg, 0.16 mmol) in anhydrous acetonitrile (1 ml). After being stirred at room temperature for 17 hours, under nitrogen, the solvent was removed under vacuum and the remaining residue was purified by flash chromatography (silica gel, dichloromethane-methanol-ammonia 95:5:0.5) to give 295 mg (83%) of the title compound as an oil; $\delta_H$ (250 MHz, CDCl$_3$) 8.00 (1H, d, J=8.5 Hz), 7.57 (1H, s), 7.42 (1H, m), 7.26 (2H, m), 6.86 (2H, m), 5.08 (2H, s), 3.79 (3H, s), 3.15 (2H, s), 2.80 (2H, m), 2.35 (6H, s), 1.72 (9H, s); m/z (CI) 468 (M+ +1). (Found: C, 66.70; H, 7.17; N, 8.86. C$_{26}$H$_{33}$N$_3$O$_5$ requires: C, 66.79; H, 7.11; N, 8.99%).

3. N,N-Dimethyl-2-[5-(4-methoxybenzyl)oxycarbonyl(3-amino-1,2,4-thiadiazol-5-yl)methyl-1-tert-butyloxycarbonylindazol-3-vl]ethylamine To a cooled (0° C.) and stirred solution of the preceding ester (286 mg, 0.61 mmol) in anhydrous dimethylformamide (5 ml) was added sodium hydride (60% dispersion in oil, 80 mg) and the mixture was stirred for 5 minutes before a solution of 3-amino-5-chloro-1,2,4-thiadiazole (120 mg, 0.89 mmol) in anhydrous dimethylformamide (2.5 ml) was added. After further 15 minutes, the reaction was quenched with aqueous phosphate buffer (pH 7; 15 ml) and products were extracted with ethyl acetate (3×20 ml). The combined organic solutions were dried (MgSO$_4$) and concentrated. Flash chromatography of the residue (silica gel, dichloromethane-methanol 95:5 to 80:20) afforded 107 mg (31%) of the title compound; $\delta_H$ (250 MHz, CDCl$_3$) 8.02 (1H, d, J=8.5 Hz), 7.68 (1H, s), 7.47 (1H, m), 7.18 (2H, m), 6.81 (2H, m), 5.38 (1H, s), 5.16 (2H, m), 4.93 (2H, br s), 3.78 (3H, s), 3.13 (2H, m), 2.79 (2H, m), 2.35 (6H, s), 1.70 (9H, s).

4.

N,N-Dimethyl-2-[5-(3-amino-1,2,4-thiadiazol-5-yl)methyl-1H-indazol-3-yl]ethylamine. Oxalate A solution of the preceding product (132 mg, 0.23 mmol) in a mixture of dichloromethane (5 ml), water (0.2 ml) and trifluoroacetic acid (1 ml) was stirred at room temperature for 30 minutes. Solvents were removed under vacuum and the remaining residue was azeotroped with a mixture of toluene and methanol (4:1; 2×20 ml). The residue was then dissolved in methanol, refluxed for 2 minutes and the methanol was removed under vacuum. The resulting oil was chromatographed over neutral alumina (grade 2.5) (ethyl acetate-methanol 95:5 to 85:15) to give the title compound and N,N-dimethyl-2-[5-(3-amino-1,2,4-thiadiazol-5-yl)methyl-1-tert-butyloxycarbonylindazol-3-yl]ethylamine. The later product was treated under the same conditions as above to produce more of the title compound as a white solid (combined yield: 39 mg, 55%). The hydrogen oxalate salt was prepared and recrystallised from ethanol-diethyl ether; mp 217°-218° C.; $\delta_H$ (360 MHz, DMSO-d$_6$) 7.75 (1H, s), 7.47 (1H, d, J=8.5 Hz), 7.32 (1H, d, J=8.5 Hz), 6.58 (2H, br s), 4.38 (2H, s), 3.16 (2H, m), 3.13 (2H, m), 2.57 (6H, s); m/z (FAB) 303 (M$^+$ +1). (Found: C, 48.99; H, 5.08; N, 21.83. C$_{14}$H$_{18}$N$_6$S 1.0 C$_2$H$_2$O$_4$ requires: C, 48.97; H, 5.14; N, 21.40%).

EXAMPLE 6

Tablet Preparation

Tablets containing 1.0, 2.0, 25.0, 26.0, 50.0 and 100.0 mg respectively of the following compounds are prepared as illustrated below:

2-[5-(3-methyl-1,2,4-oxadiazol-5-yl)-1H-indazol-3-yl]ethylamine hydrogen oxalate;

N,N-dimethyl-2-[5-(3-methyl-1,2,4-oxadiazol-5-yl)-1H-indazol-3-yl]ethylamine hydrogen oxalate.

| TABLE FOR DOSES CONTAINING FROM 1-25 MG OF THE ACTIVE COMPOUND | | | |
|---|---|---|---|
| | Amount-mg | | |
| Active Compound | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26-100 MG OF THE ACTIVE COMPOUND | | | |
|---|---|---|---|
| | Amount-mg | | |
| Active Compound | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets.

What is claimed is:

1. A compound of formula I:

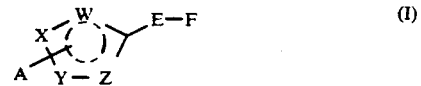

wherein the broken circle represents two non-adjacent double bonds in any position in the five-membered ring;

W, X, Y and Z independently represent oxygen, nitrogen or carbon, provided that one of W, X, Y and Z represents oxygen and at least two of W, X, Y and Z represent nitrogen and one of W, X, Y and Z represents carbon;

A is selected from the group consisting of hydrogen, hydrocarbon having up to 18 carbon atoms, halogen, cyano, trifluoromethyl, nitro, —OR$^x$, OCOR$^x$, —ONR$^x$R$^y$, —SR$^x$, —NR$^x$R$^y$, —NR$^x$-OR$^y$, —NR$^z$NR$^x$R$^y$, —NR$^x$COR$^y$, —NR$^x$CO$_2$R$^y$, —NR$^x$SO$_2$R$^y$, —NR$^z$CVNR$^x$R$^y$, —COR$^x$, —CO$_2$R$^x$ and —CONR$^x$R$^y$;

E represents a bond or a straight or branched alkylene chain containing from 1 to 4 carbon atoms;

F represents a group of formula:

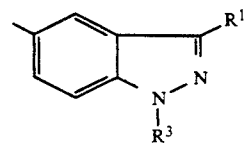

R$^1$ represents —CH$_2$.CHR$^4$.NR$^x$R$^y$ or a group of formula

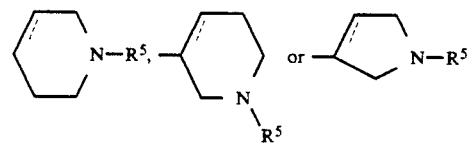

in which the broken line represents an optional chemical bond;

R$^3$, R$^4$, R$^5$ are independently selected from the group consisting of hydrogen, C$_{1-6}$alkyl, C$_{2-6}$alkenyl and C$_{2-6}$alkynyl;

R$^x$ and R$^y$ independently represent hydrogen or hydrocarbon having up to 18 carbon atoms or R$^x$ and R$^y$ together represent a C$_{2-6}$ alkylene group;

R$^z$ represents hydrogen or hydrocarbon having up to 18 carbon atoms;

V represents oxygen, sulphur or a group of formula =N.G; and

G represents hydrocarbon having up to 18 carbon atoms or an electron-withdrawing group selected from the group consisting of cyano, nitro, —COR$^x$, —CO$_2$R$^x$ and —SO$_2$R$^x$ wherein R$^x$ is as defined above and salt thereof.

2. The compound according to claim 1 represented by formula IIA:

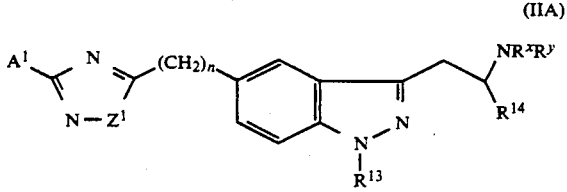

wherein $Z^1$ represents oxygen;

n is zero, 1, 2 or 3;

$A^1$ is selected from the group consisting of $C_{1-6}$ alkyl, $C_{2-6}$ alkenyl, $C_{2-6}$ alkynyl, $C_{3-7}$ cycloalkyl, aryl, aryl($C_{1-6}$)alkyl, $C_{3-7}$ heterocycloalkyl, heteroaryl and heteroaryl ($C_{1-6}$)alkyl, any of said groups may be optionally substituted; or hydrogen, halogen, cyano, trifluoromethyl, nitro, $C_{1-6}$ alkoxy, $C_{1-6}$ alkylthio, $—NR^xR^y$ or $—CONR^xR^y$;

$R^{13}$ and $R^{14}$ are independently selected from the group consisting of hydrogen, $C_{1-6}$ alkyl, $C_{2-6}$ alkenyl and $C_{2-6}$ alkynyl; and $R^x$ and $R^y$ independently represent hydrogen or hydrocarbon or $R^x$ and $R^y$ together represent a $C_{2-6}$ alkylene group.

3. The compound according to claim 1 represented by formula IIB:

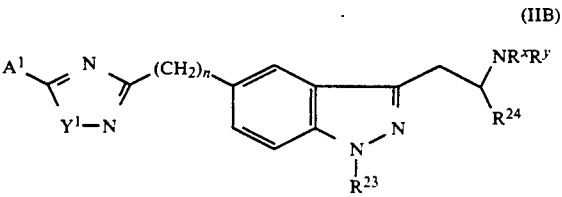

wherein $Y^1$ represents oxygen;

n is zero, 1, 2 or 3; and $A^1$ is selected from the group consisting of $C_{1-6}$ alkyl, $C_{2-6}$ alkenyl, $C_{2-6}$ alkynyl, $C_{3-7}$ cycloalkyl, aryl, aryl($C_{1-6}$)alkyl, $C_{3-7}$ heterocycloalkyl, heteroaryl and heteroaryl ($C_{1-6}$)alkyl, any of said groups may be optionally substituted; or hydrogen, halogen, cyano, trifluoromethyl, nitro, $C_{1-6}$ alkoxy, $C_{1-6}$ alkylthio, $—NR^xR^y$ or and $—CONR^xR^y$;

$R^{23}$ and $R^{24}$ are independently selected from the group consisting of hydrogen, $C_{1-6}$ alkyl, $C_{2-6}$ alkenyl and $C_{2-6}$ alkynyl; and $R^x$ and $R^y$ independently represent hydrogen or hydrocarbon, or $R^x$ and $R^y$ together represent a $C_{2-6}$ alkylene group.

4. The compound according to claim 1 represented by formula IID:

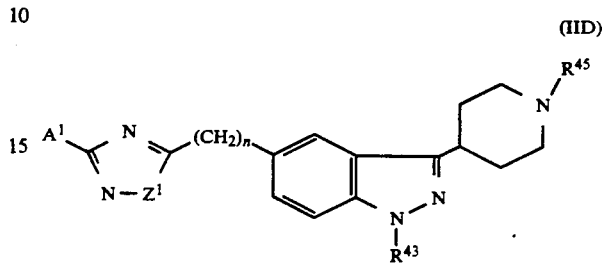

wherein $Z^1$ represents oxygen, n is zero, 1, 2 or 3; and $A^1$ is selected from the group consisting of $C_{1-6}$ alkyl, $C_{2-6}$ alkenyl, $C_{2-6}$ alkynyl, $C_{3-7}$ cycloalkyl, aryl, aryl($C_{1-6}$)alkyl, $C_{3-7}$ heterocycloalkyl, heteroaryl and heteroaryl ($C_{1-6}$)alkyl, any of said groups may be optionally substituted; or hydrogen, halogen, cyano, trifluoromethyl, nitro, $C_{1-6}$ alkoxy, $C_{1-6}$ alkylthio, $—NR^xR^y$ or and $—CONR^xR^y$;

$R^{43}$ and $R^{45}$ are independently selected from the group consisting of hydrogen, $C_{1-6}$ alkyl, $C_{2-6}$ alkenyl and $C_{2-6}$ alkynyl; and $R^x$ and $R^y$ independently represent hydrogen or hydrocarbon, or $R^x$ and $R^y$ together represent a $C_{2-6}$ alkylene group.

5. A pharmaceutical composition comprising an effective amount of a compound according to claim 1 in association with a pharmaceutically acceptable carrier or excipient.

6. A method for the treatment of clinical conditions for which a selective agonist of 5-HT$_1$-like receptors is indicated, which comprises administering to a patient in need of such treatment an effective amount of a compound according to claim 1.

7. The compound according to claim 1 selected from the group consisting of
2-[5-(3-methyl-1,2,4-oxadiazol-5-yl)-1H-indazol-3-yl]ethylamine and
N,N-dimethyl-2-[5-(3-methyl-1,2,4-oxadiazol-5-yl)-1H-indazol-3-yl]ethylamine.

* * * * *